(12) United States Patent
Woolston

(10) Patent No.: US 7,195,613 B2
(45) Date of Patent: Mar. 27, 2007

(54) INJECTION DEVICE

(75) Inventor: Robert Woolston, Moreton Morrell (GB)

(73) Assignee: DCA Design International Limited, Warwick (GB)

( * ) Notice: Subject to any disclaimer, the term of this patent is extended or adjusted under 35 U.S.C. 154(b) by 44 days.

(21) Appl. No.: 10/471,729

(22) PCT Filed: Mar. 26, 2002

(86) PCT No.: PCT/GB02/01430

§ 371 (c)(1),
(2), (4) Date: Sep. 15, 2003

(87) PCT Pub. No.: WO02/076536

PCT Pub. Date: Oct. 3, 2002

(65) Prior Publication Data

US 2004/0097879 A1 May 20, 2004

(30) Foreign Application Priority Data

Mar. 27, 2001 (GB) ................................ 0107607.4

(51) Int. Cl.
*A61M 37/00* (2006.01)
(52) U.S. Cl. .................................................. 604/154
(58) Field of Classification Search ............... 604/65, 604/66, 67, 131, 154, 156, 315; 128/DIG. 1, 128/DIG. 12, DIG. 13
See application file for complete search history.

(56) References Cited

U.S. PATENT DOCUMENTS 3,197,285 A * 7/1965 Rosen ........................ 422/100
3,800,984 A * 4/1974 Phelan ........................ 422/100
3,935,883 A * 2/1976 Stach et al. .................... 141/27
5,499,972 A * 3/1996 Parsons ........................ 604/68
6,450,082 B1 * 9/2002 Sawdon ........................ 92/23

FOREIGN PATENT DOCUMENTS

| WO | WO 98/01173    | 1/1998 |
| WO | WO 99/21598    | 5/1999 |
| WO | WO/01/23020 A2 | 4/2001 |
| WO | WO 01/23020 A3 | 4/2001 |

* cited by examiner

*Primary Examiner*—Manuel Mendez
(74) *Attorney, Agent, or Firm*—Oliff & Berridge, PLC

(57) ABSTRACT

Injection devices are known for the self administration of medicament by patients, in which the medicament is typically contained within a cartridge located within the injection device. It is a problem that injection devices should be small enough to fit into a jacket pocket or a hand bag without difficulty. Also, the injection device must be of a size that enables a piston or the like used to drive the cartridge bung within the cartridge to be moved both to a maximum dispense position within the cartridge and to be fully withdrawn from the cartridge to allow for replacement of the cartridge. A drive mechanism for an injection device is disclosed in which a piston 42 comprises a first piston part 44 guided for linear movement to selectively drive a bung 18 and a second piston part 46 connected for pivoting movement with respect to the first piston part 44.

11 Claims, 2 Drawing Sheets

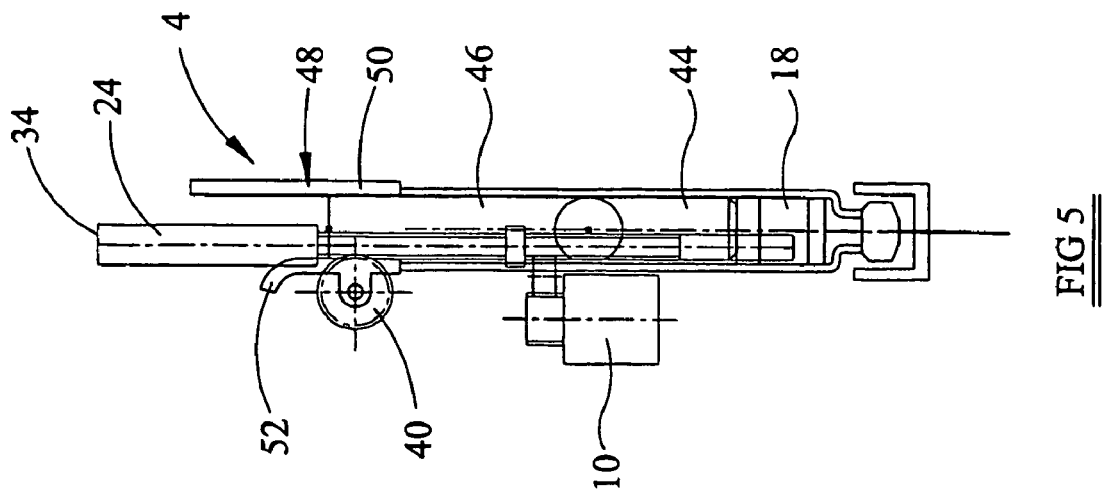
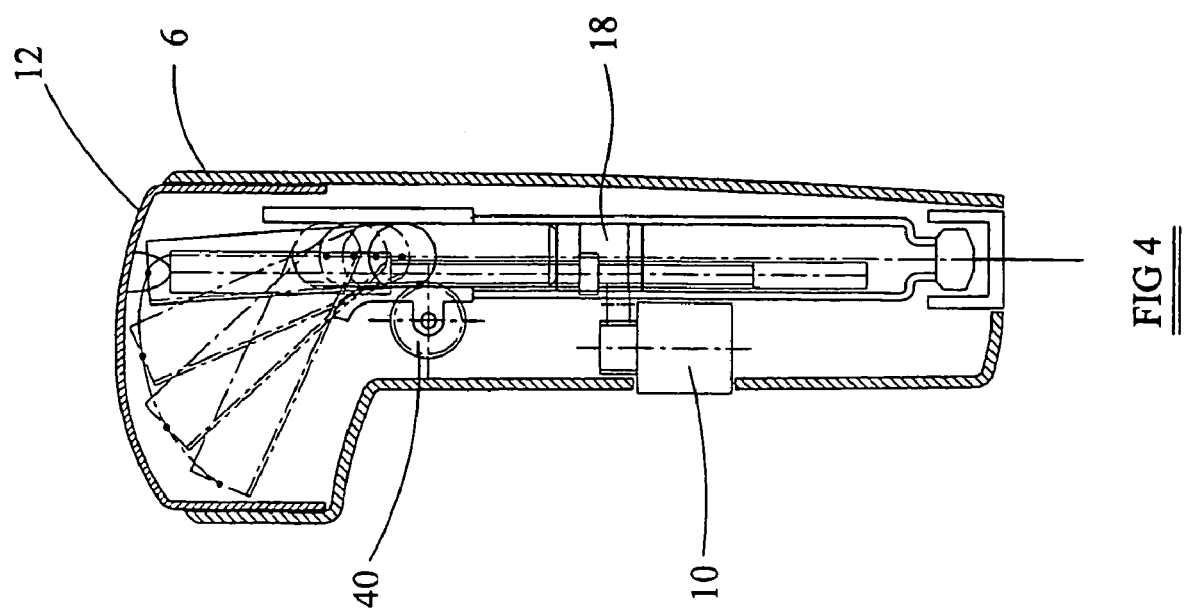

INJECTION DEVICE

The present invention relates to improvements in an injection device, and in particular to improvements in a portable injection device for dispensing controlled quantities of a medicament.

Injection devices are known for the self administration of medicament by patients. For example, those suffering from diabetes may require regular injections of insulin. Injection devices allow the patient to select a dose and to administer that dose. It is known to automate this process so that a user need only press a button and the injection device will dispense a selected dose of medicament. This relieves the patient of the task of controlling the amount dispensed while manually expelling the medicament from the injection device. This is a particular problem for the elderly, the infirm, those suffering from vision difficulties and others suffering from diabetes related problems which impair their faculties.

The medicament is typically contained within a cartridge located within the injection device. The cartridge has a bung or piston at one end which is driven towards a second end of the cartridge to expel the medicament from the injection device. It is a problem that injection devices should be small enough to fit into a jacket pocket or a hand bag without difficulty. At the same time, the injection device must be of a size that enables a piston or the like used to drive the cartridge bung within the cartridge to be moved both to a maximum dispense position within the cartridge and to be fully withdrawn from the cartridge to allow for replacement of the cartridge.

It is an advantage of the present invention that it seeks to provide a solution to these conflicting requirements.

According to a first aspect of the present invention, a drive mechanism for an injection device in which a piston is successively moved in relation to a first end of a medicament cartridge containing a medicament selectively to drive a bung closing a first end of the medicament cartridge into the medicament cartridge to expel medicament through a delivery member located at a second end of the medicament cartridge, is characterised in that the piston comprises a first piston part guided for linear movement to selectively drive the bung and a second piston part connected for pivoting movement with respect to the first piston part.

Preferably, the drive mechanism further comprises a transmission means between a dial dose mechanism and the piston.

Preferably, the transmission means comprises a dose setting mechanism connected to drive the piston through a dispense gear. More preferably, the dose setting mechanism comprises a spline connecting a dosing shaft to the dial dose mechanism, the dosing shaft having a first abutment surface at a second end. Even more preferably, the button has a stop surface for abutment with the abutment surface of the dosage shaft.

According to a second aspect of the present invention, an injection device incorporates a drive mechanism according to the first aspect of the invention.

The invention will now be described, by way of example only, with reference to the accompanying drawings in which:

FIG. 4 shows a view similar to FIG. 3 after delivery of the required dosage; and FIG. 5 shows a side section of a mechanism for use with the injection device of FIGS. 1 to 4.

Like reference numerals will be used to refer to like parts of the injection device.

Figure 1:
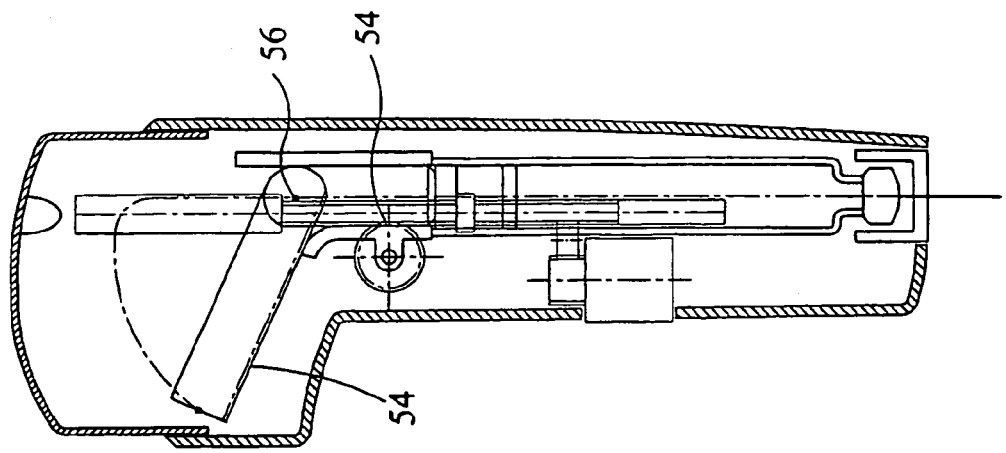
FIG. 1 shows in side section an injection device having a delivery device according to the present invention.

Referring first to FIG. 1, there may be seen an injection device 2 incorporating a drive mechanism 4 in accordance with the present invention.

The injection device 2 comprises a main housing 6, the drive mechanism 4 including a dial dose mechanism 10, and a button 12. A needle unit 14 including a delivery member in the form a hollow needle is secured to a first end of the main housing 6. A medicament cartridge 16 having a first end and a second end may be stored in the main housing 6. When the needle unit 14 is in place, the needle unit pierces a flexible membrane at the first end of the medicament cartridge 16. A displaceable bung 18 is located at the second end of the medicament cartridge 16. A cover (not shown) may be provided over the first end of the main housing 6 to protect the needle unit from damage and a user from inadvertent pricking by the needle.

The button 12 is preferably in the form of a cup or cap adapted for slidable movement within the main housing as shown in the illustrated embodiment. The main housing 6 and the button 12 are preferably provided with a catch (not shown) releasably to retain the button 12 in a closed or 'off' position. The button 12 is provided with a stop member 20 extending from an inner side of the button 12.

The dial dose mechanism 10 is located towards the first end of the main housing 6. The dial dose mechanism 10 is used by a user to select a dosage of medicament to be dispensed from the injection device in a manner to be described. The dose dial mechanism 10 is located adjacent a dose setting mechanism The dose dial mechanism 10 is connected to the dose setting mechanism by way of a gear arrangement 22.

The dose setting mechanism comprises a dosing shaft 24 having a radially extending flange 26 about a portion intermediate between a first end of the dosing shaft 24 and a second end of the dosing shaft 24. The radially extending flange 26 has a first surface which in use may abut an abutment surface provided within the main housing 6. A spline 30 is provided about the first end of the dosing shaft 24 whereby the dosing shaft 24 is connected to the gear arrangement 22. The second end of the dosing shaft 24 is provided with a threaded portion 32 along at least apart thereof The second end of the dosing shaft 24 is further provided with an abutment surface 34 for abutment with the stop member 20 on the button 12.

The drive mechanism comprises a dispense gear 40 located for rotation within the main housing 6, a piston 42 having a first piston part 44 and a second piston part 46 and guide means 48 located within the main housing 6. The guide means 48 comprises a fist rectilinear portion 50 and a curved portion 52. Each of the first piston part 44 and the second piston part 46 are provided with a toothed or threaded portion 54 along at least one side thereof. The first piston part 44 and the second piston part 46 are pivotally connected to one another about a pivot point 56.

In FIG. 1, the injection device 2 is shown with a full medicament cartridge 16 with the drive mechanism a fully retracted position and the button 12 fully depressed. The dispense gear 40 engages both the threaded portion 32 of the dosing shaft 24 and the threaded or toothed region 54 of the first piston part 44.

Figure 2:
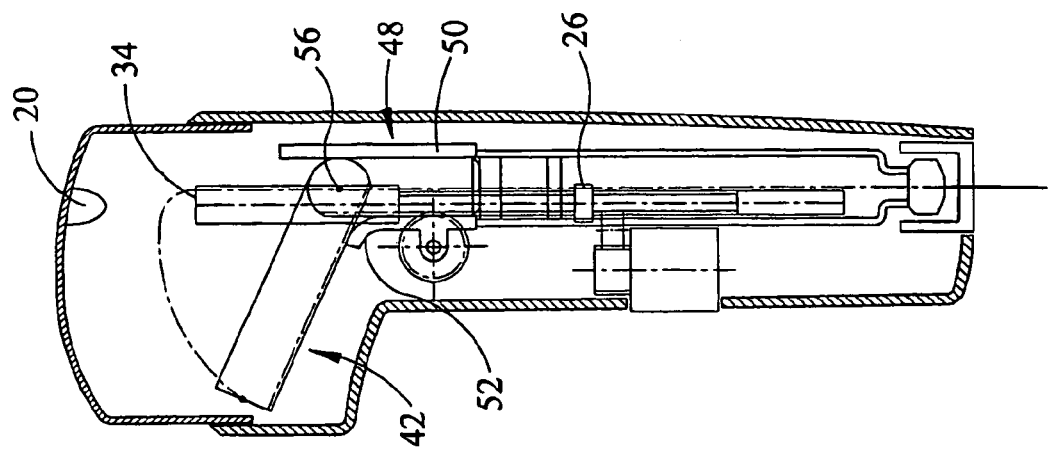
FIG. 2 shows a similar view to FIG. 1 with the injection device in ready position.

To operate the injection device 2 a user releases the button 12 from the retained or 'off' position such that the button 12 slides outwardly from within the main housing 6 (FIG. 2).

Figure 3:
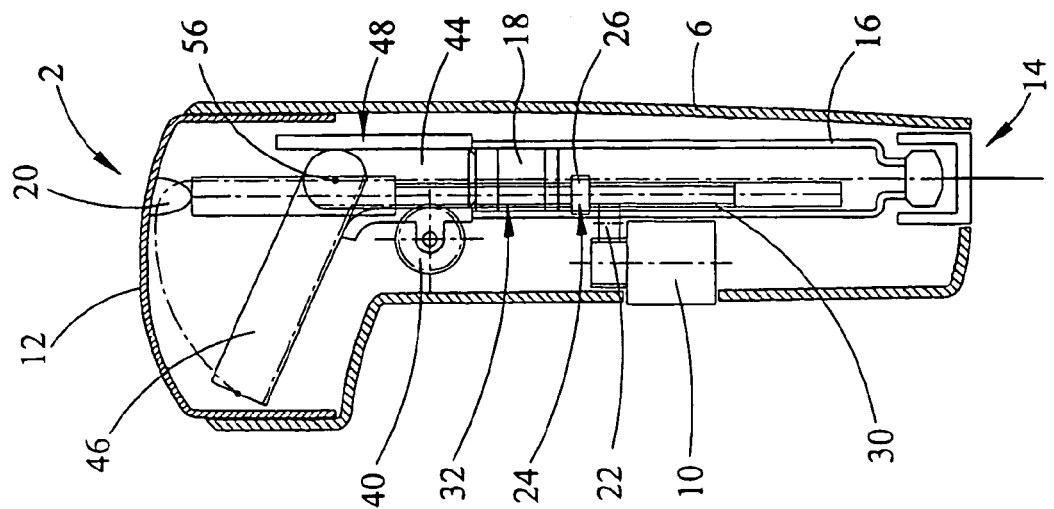
FIG. 3 shows a view similar to FIG. 2 after dialling of a required dosage.

To set a required dosage a user sets a dose using the dose dial mechanism 10. This causes the gear arrangement 22 to precess the dosing shaft 24 with respect to the spline 30 thereby moving the abutment surface 34 of the dosing shaft 24 towards the stop member 20 on the button 12 (FIG. 3).

The user can now operate the injection device to deliver the dosage set by depressing the button 12. As the button 12 is displaced within the main housing 6, the stop member 20 on the inside of the button 12 comes into contact with the abutment surface 34 of the dosing shaft 24.

Further displacement causes the dosing shaft 24 to be driven towards the first end of the injection device 2. This further displacement causes the dispense gear 40 to be rotated due to the travel of the threaded portion 42 of the dosing shaft 24. The rotation of the dispense gear 40 causes the toothed or threaded portion 54 of the first piston part 44 to be driven towards the displaceable bung 18. This in turn causes rotation of the second piston part 46 about the linearly displaced pivot point 56 as the first piston part 44 is driven into the rectilinear portion 50 of the guide means 48. Concurrently, the second piston part 46 is guided by the curved portion 52 of the guide means 48 towards and into the rectilinear portion 50 of the guide means by the action of the first piston part 44. It will be seen that a swinging movement of a free end of the second piston part 46 occurs within the fully retracted position of the button 12 (FIG. 4). The further displacement of the dosing shaft 24 continues until the button 12 has been fully depressed.

On the next use of the injection device 2, a new dose is set, precessing the dosing shaft 24 further prior to depression of the button 12. As the process is repeated the first piston part 44 is driven further into the rectilinear portion 50 of the guide means, such that the first piston part 44 passes beyond the dispense gear 40. At this point, the dispense gear 40 engages with the toothed or threaded region 54 of the second piston part 46 to drive the second piston part 46. The first piston part 44 is then driven towards the displaceable bung 18 under the action of the second piston part 46.

This process is repeated until replacement of the medicament cartridge 16 is required (FIG. 5). The first piston part 44 and the second piston part 46 can then be withdrawn from the medicament cartridge 16 under the action of the dispense gear 40 to allow subsequent replacement of the medicament cartridge 16.

The relative an arrangement of the drive mechanism and the medicament cartridge means that the main housing provides a relatively large flat face where a relatively large dose display, such as a liquid crystal display may be located. This in turn enables the dose display to use relatively large figures or other characters. This is an advantage for those with impaired vision.

The invention claimed is:

1. A drive mechanism for an injection device, comprising:
a piston that is successively moved in relation to a first end of a medicament cartridge containing a medicament selectively to drive a bung closing a first end of the medicament cartridge into the medicament cartridge to expel medicament through a delivery member located at a second end of the medicament cartridge, the piston further comprising:
a first piston part guided for linear movement to selectively drive the bung; and
a second piston part connected for pivoting movement with respect to the first piston part,
wherein the piston is driven through a dispense gear by a dosing shaft.

2. A drive mechanism according to claim 1, further comprising a transmission mechanism between a dial dose mechanism and the piston.

3. An injection device incorporating a drive mechanism according to claim 2.

4. A drive mechanism according to claim 2, wherein the transmission mechanism comprises a dose setting mechanism connected to drive the piston through the dispense gear.

5. An injection device incorporating a drive mechanism according to claim 4.

6. A drive mechanism according to claim 4, wherein the dose setting mechanism comprises a spline connecting the dosing shaft to the dial dose mechanism, the dosing shaft having an abutment surface at one end.

7. An injection device incorporating a drive mechanism according to claim 6.

8. A drive mechanism according to claim 6, wherein a button has a stop surface for abutment with the abutment surface of the dosing shaft.

9. An injection device incorporating a drive mechanism according to claim 8.

10. An injection device incorporating a drive mechanism according to claim 1.

11. An injection device according to claim 10, further comprising a drive means selectively to drive the bung having a button displaceably housed in the injection device.

* * * * *